United States Patent [19]
Höfle et al.

[11] Patent Number: 5,622,979
[45] Date of Patent: Apr. 22, 1997

[54] THIANGAZOLE, ITS PREPARATION, COMPOSITIONS AND USE THEREOF

[75] Inventors: Gerhard Höfle, Braunschweig; Norbert Bedorf, Königslutter; Edgar Forche; Klaus Gerth, both of Braunschweig; Herbert Irschik, Wolfenbüttel; Rolf Jansen; Brigitte Kunze, both of Braunschweig; Hans Reichenbach, Wolfenbüttel; Florenz Sasse, Braunschweig; Heinrich Steinmetz, Hildesheim-Sorsum; Wolfram Trowitzsch-Kienast, Braunschweig, all of Germany; Johannes P. Pachlatko, Seltisberg, Switzerland

[73] Assignees: Ciba-Geigy Corporation, Tarrytown, N.Y.; Gesellschaft fur Biotechnologische Forschung mbH, Braunschweig, Germany

[21] Appl. No.: 487,384

[22] Filed: Jun. 7, 1995

Related U.S. Application Data

[60] Continuation of Ser. No. 286,309, Aug. 5, 1994, abandoned, which is a division of Ser. No. 78,159, filed as PCT/EP91/02336, Dec. 6, 1991, abandoned.

[30] Foreign Application Priority Data

Dec. 24, 1990 [DE] Germany ............... 40 41 685.2

[51] Int. Cl.$^6$ ................... A01N 43/78
[52] U.S. Cl. ................... 514/365
[58] Field of Search ................... 514/365

[56] References Cited

U.S. PATENT DOCUMENTS

| | | | |
|---|---|---|---|
| 3,651,216 | 3/1972 | Ringel et al. | 514/365 |
| 4,175,126 | 11/1974 | Lombardi et al. | 514/365 |
| 4,560,690 | 12/1985 | Reiter | 514/365 |

FOREIGN PATENT DOCUMENTS

| | | |
|---|---|---|
| 0162841 | 11/1985 | European Pat. Off. . |
| 0282455 | 7/1988 | European Pat. Off. . |
| 2399247 | 3/1979 | France . |
| 3823067 | 1/1990 | Germany . |
| 8000573 | 4/1980 | WIPO . |

OTHER PUBLICATIONS

Gesellschaft für Biotechnologische Forschung mbH, Wissenschaftlicher Ergebnisbericht 1990 ("Report on Scientific Results" 1990) pp. 52–55.

March, Advanced Organic Chemistry 3rd ed., pp. 109–113 (1985).

*Primary Examiner*—Robert Gerstl
*Attorney, Agent, or Firm*—Marla J. Mathias; William A. Teoli, Jr.

[57] ABSTRACT

The invention relates to compounds of the following general formula I

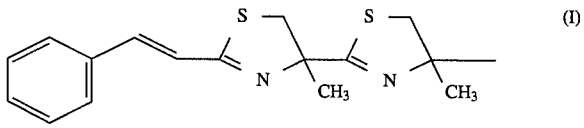

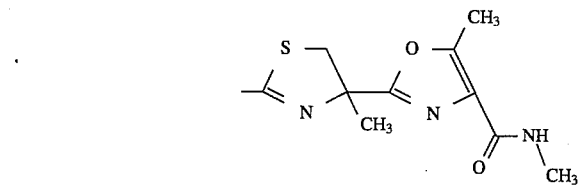

especially the compound of formula Ia referred to as thiangazole

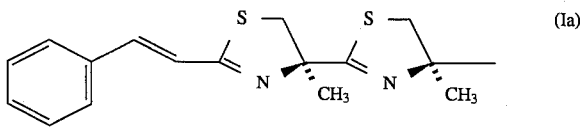

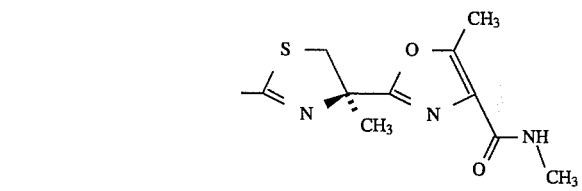

their pharmaceutically acceptable acid addition salts, processes for their preparation and therapeutic compositions and compositions that can be used in crop-protection.

3 Claims, No Drawings

THIANGAZOLE, ITS PREPARATION, COMPOSITIONS AND USE THEREOF

This is a continuation of Ser. No. 08/286,309, filed Aug. 5, 1994, abandoned which is a division of Ser. No. 08/078, 159, 35 USC 371 date Sep. 17, 1993, abandoned, which is a 371 of PCT/EP91/02336, filed Dec. 6, 1991.

The present invention relates to compounds of formula I below and, among those, especially the compound of formula Ia called thiangazole, and to the pharmaceutically acceptable acid addition salts of compounds of formulae I and Ia. It relates also to pharmaceutical compositions (with the exception of those against viral diseases) that comprise one of those compounds together with customary formulation adjuvants. Compositions that comprise one of the compounds of formula I or Ia are suitable for controlling Arthropoda and Acarina and also for controlling parasitic diseases in humans, animals and plants. Special mention should be made of their anthelmintic, acaricidal and insecticidal activity. In addition to the pharmaceutical compositions, the invention therefore relates also to pesticides based on compounds of formula I or Ia. It relates also to the preparation of the active ingredients and of the said compositions and to their use for controlling parasites in humans, animals and plants, especially for controlling helminths, especially nematodes, cestodes and trematodes in warm-blooded animals, especially in domestic animals and productive livestock, and to their use for controlling pests of the order Arthropoda, preferably for controlling insects and representatives of the order Acarina.

The present invention relates especially to compounds of the following general formula I and to their pharmaceutically acceptable acid addition salts:

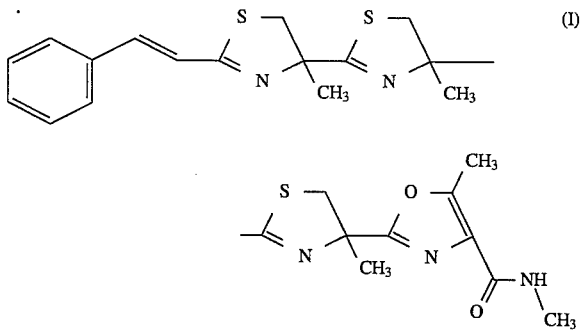

and especially to the compound of formula Ia referred to as thiangazole

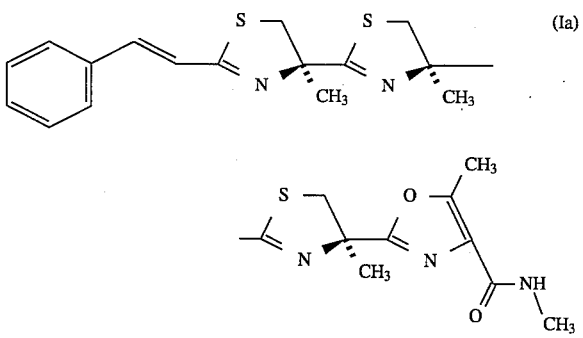

and to its pharmaceutically acceptable acid addition salts.

That thiangazole is obtainable by culturing the myxobacterium Polyangium spec. DSM 6267 (deposited under Budapest Treaty with DSM Deutsche Sammmlung von Mikroorganismen und Zellkulturen (Braunschweig, Germany) on Dec. 11, 1990) in a medium containing carbon sources, nitrogen sources and mineral salts, extracting the harvested cell mass with
acetone,
concentrating the (combined) extract,
taking up the concentrate in ether/water,
separating off the aqueous phase and if necessary extracting with ether,
concentrating the (combined) ethereal phase,
taking up the concentrate in methanol/heptane,
separating off the methanol phase and if necessary extracting with heptane,
then concentrating and extracting with tert-butyl methyl ether,
filtering the extract in tert-butyl methyl ether over Florisil,
crystallising thiangazole (or antibiotic and/or fungicidal activity) from the extract and
if appropriate converting the thiangazole (or antibiotic and/or fungicidal activity) into a therapeutically acceptable acid addition salt.

The thiangazole produced by the myxobacterium Polyangium spec. DSM 6267 has the configuration shown in formula Ia. Cis-trans isomers of the thiangazole of the general formula I given above are obtainable by subjecting the thiangazole obtainable by the process indicated to heat treatment or to treatment with UV light.

All the compounds of the invention can be convened in a manner known per se into pharmaceutically acceptable acid addition salts.

Compounds of formulae I and Ia can also be in the form of salts, especially pharmaceutically acceptable, that is to say physiologically tolerable, salts. Pharmaceutically unacceptable salts can also be used for isolation or purification purposes. Only pharmaceutically acceptable salts are used therapeutically and these are therefore preferred.

Pharmaceutically acceptable acid addition salts are to be understood as being those that are not disadvantageous physiologically. They are physiologically tolerable addition compounds, especially complexes and salts of a compound of formula I with an inorganic or organic base which are formed by the addition of an equivalent mount of a salt-forming base to the basic molecule of formula I or with solvents such as dimethylformamide (DMF) or dimethylacetamide (DMA). There are suitable especially metal salts or ammonium salts, such as alkali metal and alkaline earth metal salts, for example sodium, potassium, magnesium or calcium salts, or ammonium salts with ammonia or with suitable organic mines, especially tertiary monoamines and heterocyclic bases, for example trialkylamines, such as triethylamine or dialkylamines, such as diethylamine or dipropylamine, or other organic bases such as N,N'-dimethylpiperazine.

Furthermore, a preferred embodiment of the invention relates to therapeutic compositions (with the exception of those against viral diseases) that consist of a compound of the invention as active ingredient or comprise such a compound of the invention together with a customary carrier and/or diluent. Compounds of the invention are to be understood in this context to include pharmaceutically acceptable acid addition salts. Those compositions are suitable for controlling parasitic diseases in humans and animals.

The present invention relates also to a compound, preferably of the thiangazole type, which is characterised by one or more of the parameters given in claim 3.

The invention is explained in detail below using experimental data:

A. Production conditions

A.1. Production strain: the bacterium Polyangium spec. Strain P1 3007 order Myxobacteriales, suborder Sorangineae, family Polyangiaceae.

A.2. Origin of production strain: isolated at GBF, Gesellschaft für Biotechnologische Forschung mbH (Brunswick/Germany), in October 1986 from soil from the gardens of the Alhambra, Granada, Spain.

A.3. Description of production strain: the vegetative cells are cylindrical with broadly curving ends (Polyangium type), generally about 0.6–0.8×4–6 μm. In the event of nutrient deficiency, for example when cultured on a smear of living *Escherichia coli* bacteria on water-agar, the organism forms fruiting bodies. These are plate-like piles of small to medium-sized, spherical or ovoid, gold- to red-brown sporangioles the diameter of which is generally about 30–80 μm. The sporangiole piles may become very large, but vary greatly in extent, generally from 100 to 600 μm. P1 3007 grows well on living *Escherichia coli* bacteria on water-agar, the feedstuff bacteria being broken down. The gliding movement of the bacterial cells causes the colony gradually to spread out in a swarm over the culture plate. In addition, the organism also grows well on yeast-agar (VY/2 agar: 0.5% baker's yeast; 0.1% $CaCl_2.2H_2O$; 0.5 mg/l cyanocobalamine; pH 7.2). As it grows, it penetrates deep into the culture substrate and breaks down the yeast cells to a considerable extent. Catalase and oxidase are positive. In liquid media the strain grows in small clumps of cells both in shaken flasks at 160 rpm (100 ml of medium in a 250 ml Erlenmeyer flask or 500 ml of medium in a 1000 ml Erlenmeyer flask), as well as in bioreactors (tested up to a scale of 300 liters). An example of a suitable culture medium is Poll medium: Probion PS (single-cell protein from *Methylomonas clarae*; Hoechst, Frankfurt) 0.4%; starch 0.3%; $MgSO_4.7H_2O$ 0.1%; $CaCl_2.2H_2O$ 0.05%; 1 ml/l standard trace-element solution (G. Drews, Messbiologisches Praktikum, 2nd edition, p. 6, Springer Verlag, Berlin 1974) and 1 ml/l standard vitamin solution (H. G. Schlegel, Allgemeine Mikrobiologie, 6th edition, page 174, Thieme-Vertag, Smugan 1985); pH 7.0. The cultures are kept at 30° C. for 3–4 days. P1 3007 can be preserved: for example by freezing vegetative cells from agar plates or liquid cultures in peptone solution at −80° C. or in liquid nitrogen.

A.4. Performance of the production strain: An activity can be detected in cell extracts or to a certain extent also in XAD eluates of P1 3007 that inhibits the growth of certain fungi in an agar diffusion test (see below). Chemically the substance consists inter alia of 3 thiazoline nuclei and one oxazole nucleus and has been named thiangazole.

A.5. Availability of the strain: The production strain has been deposited with the Deutsche Sammlung von Mikroorganismen in Brunswick as a patent strain under No. DSM 6267.

A.6. Detection of thiangazole: For qualitative detection of thiangazole cell masses are extracted with acetone or the cultures are stirred with the adsorber resin XAD 1180 (Messrs. Rohm and Haas) and the XAD batches are eluted with methanol and acetone after sieving. Aliquots of the concentrated extracts are tested for inhibition, for example of the fungus *Mucor hiemalis*, and in a thin-layer chromatography test thiangazole is identified by comparison with the pure substance. The working up, isolation and chemical characterisation are effected in accordance with Section B.

A.7. Production conditions of thiangazole: In shaken flasks thiangazole is formed during growth and reaches its highest activity from the end of the logarithmic phase to the early stationary phase.

B. Fermentation in a bioreactor

Bioreactor (b50) having a capacity of 65 liters from Messrs. Giovanola Frères, Monthey, Switzerland, with two paddle stirrers. Medium: Probion PSC/single-cell protein from *Methylomonas clarae*; Hoechst, Frankfurt) 0.4%; starch 0.3%; $MgSO_4.7H_2O$ 0.1%; $CaCl_2.2H_2O$ 0.05%; standard trace-element solution 1 ml/liter (see above) and cyanocobalamine 0.5 mg/liter; pH 7.2. 60 liters of medium are inoculated with 5 liters of culture from a shaken flask having a good culture growth. The aeration rate is set at 200 Nl/hour and the speed at 200 rpm. The $pO_2$, which is at 100% saturation at the start of fermentation, falls continuously to 85% by the end of fermentation after 95 hours. The pH value rises over the course of the fermentation from 7.0 to 7.2. (Nl denotes normal liter=1 liter of air under normal conditions.)

Isolation of thiangazole 309 g of moist Polyangium P1 3007 cell mass are stirred with 500 ml of acetone. The solid residue is centrifuged off and extracted four times for 30 minutes with approximately 150 ml of acetone each time and then centrifuged off. The combined acetone supernatants are concentrated in vacuo. The residue (6.7 g) is dissolved in ether/water. The aqueous phase is extracted three times with ether and discarded. The combined ethereal phases are concentrated in vacuo (3.54 g) and dissolved in methanol/heptane. After removal of the heptane phase the methanol phase is extracted three times with heptane and concentrated in vacuo (1.93 g). The heptane phases are discarded. The crude product from the methanol phase is filtered with 500 ml of tert-butyl methyl ether over 50 ml of Florisil. The filtrate is concentrated in vacuo and petroleum ether is added. 82 mg of the product are separated in the form of crystals. The mother liquor is purified by medium-pressure chromatography (column (diameter×length) 37×420 mm, silica gel 15 μ, 60 Å (H2D-SIL-15-60, Messrs. Kronwald), eluant petroleum ether/tert-butyl methyl ether/methanol 50/49/1, 28 ml/min, detection UV absorption at 278 nm. The main peak ($t_R \approx 45$ min) is combined and crystallised in tert-butyl methyl ether/petroleum ether (35 mg).

Yield 117 mg.

Physical data of thiangazole

Detection of thiangazole by analytical HPLC: Column (diameter×length) 4×250 mm, packed with HD-SIL 18-5-100 (Messrs. Kronwald), detection UV absorption at 290 nm, eluant methanol/water (80:20), flow 1.5 ml/min, $t_R$=5.8 min; with methanol/water (75/25) $t_R$=10.5 min.

m.p. 140° C.

UV (methanol): $\lambda_{max}$ (ϵ/lg ϵ)=211 (sh), 218 (sh), 223 (37884/4.578), 228 (sh), 288 (36384/4.561), 300 (sh). (sh=shoulder).

IR($CHCl_3$): 3432 (m), 1664 (s), 1633 (s), 1577 (m), 1567 (m), 1536 (m), 1465 (w), 1449 (w), 1413 (w), 1370 (w), 1168 (m), 1102 (m), 1015 (m), 963 (m) $cm^{-1}$–(s=strong, m=medium strength, w=low intensity).

$^1$H-NMR ($CDCl_3$, 300.133 MHz): δ=7.48 (m, 2H), 7.35 (M, 3H), 7.13 (d, 1H, J=16.2 Hz),7.04(d, 1H, J=16.2 Hz), 6.91 (m 1H),3.85(d, 1H, J=11.2 Hz),3.81 (d, 1H, J=10.6 Hz),3.74(d, 1H, J=11.4 Hz),3.37 (d, 1H, J=11.2 Hz),3.27 (d, 1H, J=11.4 Hz), 3.20(d, 1H, J=11.3 Hz),2.93 (d, 3H, J=5.1 Hz),2.63 (s, 3H), 1.68 (s, 3H), 1.66(s, 3H), 1.59 (s, 3H).

$^{13}$C-NMR ($CDCl_3$, 75.473 MHz): δ=179.22 s, 178.07 s, 167.90 s, 162.50 s, 162.36 s, 153.39 s, 141.99 d, 135.12 s, 129.73 d, 129.18 s, 128.92 d(2C), 127.62 d(2C), 122.48 d, 83.69 s, 83.53 s, 79.45 s, 43.22 t, 42.50 t, 41.99 t, 26.15 q, 25.70 q 25.53 q, 24.38 q, 11.75 q. (s, d, t and q denote the signal multiplicities that would produce an SFORD $^{13}$C-NMR spectrum. 2C denotes double signal intensity.)

(+)FAB-MS (xenon, matrix 3-nitrobenzyl alcohol): m/z= 540=(M+H)$^+$.

High resolution:
[$C_{26}H_{29}N_5O_2S_3+$] calculated 540.1562 found 540.1688 (FAB-MS)

EI-MS (210° C., 70 eV): m/z (%)=541 (2.1), 540 (5.1), 539 (14) [M$^+$], 524 (12), 493 (16), 379 (4.5), 337 (20), 301 (50), 280 (21), 260 (44), 213 (23,202 (74), 182 (18), 172 (31), 150 (14), 140 (19), 130 (22), 115 (21), 103 (10), 85 (22), 73 (100).

High resolutions:
$C_{26}H_{29}N_5O_2S_3$ calc. 539.1483 found 539.1488 (EI-MS)
$C_{25}H_{27}N_5O_2S_2$ calc. 493.1606 found 493.1604 (EI-MS)
$C_{14}H_{17}N_4O_2S_2$ calc. 337.0793 found 337.0793 (EI-MS)
$C_{16}H_{17}N_2S_2$ calc. 301.0833 found 301:0833 (EI-MS)
$C_{13}H_{12}N_2S_2$ calc. 260.0442 found 260.0444 (EI-MS)
$C_{12}H_{12}N_1S_1$ calc. 202.0690 found 202.0691 (EI-MS)

Commercial names

HD-Sil-15-50 and HD-Sil-18-5-100 (Kronwald) Florisil (Floridin Corp.; magnesium silicate gel)

C. Biological activity

It has been found, suprisingly, that the compounds according to the invention of the general formula I and especially thiangazole according to the invention of formula Ia are valuable active ingredients against parasites in humans, animals and plants while being well tolerated by warm-blooded animals, fish and plants. It not only exhibits a broad spectrum of activity against helminths, such as nematodes, cestodes and trematodes, that are parasites in the human or animal organism, especially in mammals, its activity being directed preferably against nematodes (roundworm), but can also be used successfully against phytopathogenic insects and arachnids that occur on useful plants and ornamentals in agriculture, especially in cotton, vegetable and fruit crops, in forestry, in the protection of stored goods and material stocks, and also in the hygiene sector, especially on domestic animals and productive livestock. Thiangazole is, moreover, effective against all or individual development stages of normally sensitive and also resistant species of insects and arachnids.

A special feature of the compounds of formulae I and Ia that should be mentioned is the surprising degree to which they are tolerated by warm-blooded animals, which makes them superior to many other anthelmintics. The handling of those compounds in practice in the treatment of worm-infested animals is facilitated to an extraordinary degree as a result, since even relatively high doses are tolerated by the medicated animals, without any symptoms.

The novel compounds according to the invention of formulae I and Ia are suitable as anthelmintics for example for controlling parasitic nematodes of the orders (in accordance with K. I. Skrajabin)

Rhabditida

Ascaridida

Spirurida

Trichocephalida or for controlling cestodes of the orders (in accordance with Wardle and McLeod)

Cyclophyllidae

Pseudophyllidae or for controlling trematodes of the order

Digenea in domestic animals and productive livestock, such as cattle, sheep, goats, horses, pigs, red deer, cats, dogs and poultry. Thiangazole can be administered to the animals in a single dose or in repeated doses, the individual doses preferably being from 1 to 50 mg per kg of body weight, according to the species of animal. With protracted administration it is possible in some cases to achieve a better effect or for lower total doses to suffice.

In the case of animal pests from the group of the Insecta and Acarina, the action of the compounds according to the invention of formulae I and Ia may manifest itself in the death of the pests immediately or only at a later date, for example at moulting, or in reduced oviposition and/or a reduced hatching rate. The above-mentioned animal pests include:

of the order Lepidoptera, for example: Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busscola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta, Cydia* spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp, *Lobesia botrana*, Lymantria spp., Lyonefta spp., Malacosoma spp., *Mamestra brassicae, Manduca sexta*, Operophtera spp., *Ostrinia nubilalis*, Pammene spp., Pandemis spp., *Panotis flammea, Pectinophora gossypiella, Phthorhnaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tottrix spp., *Trichoplusia ni* and Yponomeuta spp.;

of the order Coleoptera, for example: Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp. Melolontha spp., Orycaephilus spp., Otiorhynchus spp., Phlyctinus spp., Popilia spp., Psylliodes spp., Rhizopertha spp., Scarabeidae, Sitophilus spp., Sitotroga spp., Tenebrio spp., Tribolium spp. and Trogoderma spp.;

of the order Orthoptera, for example: Blatta spp., Blattella spp., Gryllotalpa spp., *Leucophaea maderae*, Locusta spp., Periplaneta spp. and Schistocerca spp.;

of the order Isoptera, for example: Reticulitermes spp.;

of the order Psocoptera, for example: Liposcelis spp.;

of the order Anoplura, for example: Haematopinus spp., Linognathus spp. Pediculus spp., Pemphigus spp. and Phylloxera spp.;

of the order Mallophaga, for example: Damalinea spp. and Trichodectes spp.;

of the order Thysanoptera, for example: Frankliniella spp., Hercinothrips spp., Taeniothrips spp., *Thrips palmi, Thrips tabaci* and *Scirtothrips aurantii;* of the order Heteroptera, for example: Cimex spp., *Distantleila theobroma*, Dysdereus spp., Euchistus spp. Eurygaster spp. Leptocofisa spp., Nezara spp., Piestoa spp., Rhodrtius spp., *Sahlbergella singularis*, Scotinophara spp. and Triatoma spp.;

of the order Homoptera, for example: *Aleurothrixus floccosus, Aleyrodes brassieae*, Aonidiella spp., Aphididac, Aphis spp., Aspidioms spp., *Bemisia tabaci,* Ceroplaster spp., *Chrysomphalus aonidium, Chrysomphalus dictyospermi, Coccus hespefidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratona spp., Pemphigus spp., Planococcus spp., Pseudaulacaspis spp., Pseudococcus spp., Psylla spp., *Pulvinana aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* of the order Hymenoptera, for example: Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

of the order Diptera, for example: Aeries spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp. *Oscinella frit, Pegomyia hyoscyami,* Phorbia spp., *Rhagoletis pomonella,* Sciara spp., Stomoxys spp., Tabanus spp., Tannia spp. and Tipula spp.;

of the order Siphonaptera, for example: Ceratophyllus spp., *Xenopsylla cheopis,* of the order Acarina, for example: *Acarus siro, Acefia sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp.; and of the order Thysanura, for example: *Lepisma saccharina.*

The compounds according to the invention of formulae I and Ia are therefore very suitable for controlling pests from the group of the insects and arachnids in cotton, fruit, maize, soybean, citrus and vegetable crops. They control especially plant-eating insects such as *Anthonomus grandis,* plant-eating insect larvae such as those of *Spodoptera littoralis* or *Heliothis virescens,* sucking insects such as *Aphis craccivora* or *Bemisia tabaci* and soil insects such as *Diabrotica balteata.*

The compounds of formulae I and Ia can also be used as dressing agents for protecting seed (fruit, tubers, grains) and plant cuttings from noxious insects and from phytopathogenic noxious insects which occur in the soil.

The invention therefore relates also to compositions that comprise as active ingredient a compound of formula I or Ia, especially compositions for crop protection, and to their use in the agricultural sector, including agriculture, horticulture and forestry or related fields.

The present invention further embraces the preparation of those compositions which comprises homogeneously mixing and/or grinding the active ingredient with one or more of the substances or groups of substances described herein. The formulation steps can be supplemented by kneading, granulating (in the case of granules) and, if appropriate, compressing (in the case of pellets). Also included is a prophylactic and/or curative method for controlling pests of plants and/or helminths in the case of mammals, which comprises applying a compound according to the invention of formula I or Ia or the composition according to the invention to the locus of the pest.

Target animals to be protected by the use as anthelmintics are all warm-blooded animals that can be infested by helminths, especially all mammals including humans, and birds, but especially domestic animals, productive livestock and pets, such as cows, horses, donkeys, sheep, goats, llamas, camels, red deer, pigs, dogs, cats, rabbits, hens, turkeys, ducks, geese, pheasants, partridges, etc., as well as all fur-producing fanned animals. It is, of come, possible also to treat infested zoo animals successfully.

As is generally known, of the endoparasites occurring in warm-blooded animals, it is specifically helminths that cause great damage in the animals they infest. The damage caused by helminthiasis can assume very great economic significance where there is chronic and especially epidemic occurrence of worm-related disorders in herds of live-stock. The damage manifests itself in the diseased mammals inter alia in reductions in productivity, reduced resistance to other diseases and increased mortality. Especially dangerous worm-related disorders are brought about by helminths that parasiticise the gastro-intestinal tract and other organs and occur relatively frequently, in spite of numerous prophylactic measures, in ruminants, such as cattle, sheep and goats, and also in horses, pigs, poultry, red deer, dogs and cats.

In the present description there is to be understood by the term "helminths" especially parasitic worms that belong to the Platyhelminthes (cestodes, trematodes) and the Nemathelminthes (nematodes and related species), that is to say tape worms, sucker worms and roundworms of the gastro-intestinal tract and other organs (for example liver, lungs, kidneys, lymph vessels, blood, etc.).

One of the most pressing tasks is therefore to provide therapeutic compositions that arc suitable for controlling helminths in all stages of development and for preventing infestation by those parasites.

Although a number of substances having anthelmintic activity are known that have been proposed for controlling various species of helminth, these are not completely satisfactory, either because at a tolerable dose it is not possible to make full use of their spectrum of activity, or because at therapeutically effective doses they exhibit undesired side effects or properties. In this respect, the resistance to certain classes of substance that is occurring more and more today is also becoming increasingly significant. "Albendazole" which is described, for example, in the literature (British Pat. No. 1464326; Am. J. Vet. Res. 38, 1425–1426 (1977); Am. J. Vet. Res. 37 1515–1516 (1976); Am. J. Vet. Res. 38, 807–808 (1977); Am. J. Vet. Res. 38, 1247–1248 (1977)) has only a limited spectrum of anthelmintic activity in ruminants. Its activity against benzimidazole-resistant nematodes and adult liver flukes is totally inadequate, since in particular the pathogenically important immature migrating forms of the latter are not affected by doses tolerated by the host animal. The provision of compounds having a completely novel basic structure overcomes a large number of resistance problems.

Target crops to be protected against phytopathogenic pests within the scope of the present invention by the crop-protecting use disclosed herein comprise e.g. the following species of plants: cereals (wheat, barley, rye, oats, rice, maize, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, aubergines, sugar cane, tea, pepper, vines, hops, bananas and natural rubber plants, as well as ornamentals.

The compounds of formulae I and Ia are normally applied in the form of compositions and can be applied to the crop area or plant to be treated, simultaneously or in succession, with further compounds. These further compounds can be fertilisers or micronutrient donors or other preparations that influence plant growth. They can also be selective herbicides as well as insecticides, fungicides, bactericides, nematicides, molluscicides or mixes of several of these preparations, if desired together with further careers, surfactants or other application-promoting adjuvants customarily employed in formulation technology.

The good pesticidal activity of the compounds of formulae I and Ia according to the invention corresponds to a mortality of at least 50–60% of the mentioned pests.

The activity of the compounds of the invention and of the compositions comprising them against animal pests can be substantially broadened and adapted to prevailing circumstances by the addition of other insecticides and/or acaricides. Examples of suitable additives include representatives of the following classes of compounds: organophosphorus compounds, nitrophenols and derivatives thereof, formamidines, ureas, carbamates, pyrethroids, chlorinated hydrocarbons, and *Bacillus thuringiensis* preparations.

The compounds of formulae I and Ia are used in unmodified form or, preferably, together with the adjuvants conventionally employed in formulation technology, and can therefore be formulated in known manner e.g. into emulsifiable concentrates, directly sprayable or dilutable solutions, dilute emulsions, wettable powders, soluble powders, dusts, granules, and also encapsulations in polymer substances. As with the compositions, the methods of application, such as spraying, atomising, dusting, scattering or pouring, are chosen in accordance with the intended objectives and the prevailing circumstances.

A preferred method of applying a compound of formula I or Ia, or an agrochemical composition which comprises at least one of said compounds, is foliar application. The number of applications and the rate of application depend on the risk of infestation by the corresponding pathogen. However, the compounds of formulae I and Ia can also penetrate the plant through the room via the soil (systemic action) if the locus of the plant is impregnated with a liquid formulation, or if the compounds are applied in solid form to the soil, e.g. in granular form (soil application). In paddy rice crops, such granules may be applied in metered amounts to the flooded rice field. The compounds of formulae I and Ia may, however, also be applied to seeds (coating) either by impregnating the seeds with a liquid formulation comprising the compound, or by coating them with a solid formulation.

The formulations, i.e. the compositions, comprising as active ingredient a compound of the invention, or combinations of those compounds, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the $C_8$ to $C_{12}$ fractions of alkylbenzenes, e.g. xylene mixtures or alkylated naphthalenes, aliphatic or cycloaliphatic hydrocarbons such as cyclohexane, paraffins or tetrahydronaphthalene, alcohols such as ethanol, propanol or butanol, and glycols and their ethers and esters, such as propylene glycol, dipropylene glycol ether, ethylene glycol, ethylene glycol monomethyl or monoethyl ether, ketones such as cyclohexanone, isophorone or diacetone alcohol, strongly polar solvents such as N-methyl-2-pyrrolidone, dimethyl sulfoxide or dimethylformamide, or water, vegetable oils such as rapeseed off, castor oil, coconut off or soybean oil; and, where appropriate, silicone oils.

The solid carders used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carders are porous types, for example pumice, broken brick, sepiolite or bentonite; and suitable nonsorbent carriers are calcite or sand. In addition, a great number of granulated materials of inorganic or organic nature can be used, e.g. especially dolomite or pulverised plant residues.

Suitable surface-active compounds are the combinations of of the compounds of formula I or Ia with other insecticides or acaricides together with non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable artionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts as surfactants.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$-alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide, or phospholipids.

Non-ionic surfactants are especially polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpotyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are especially quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described, for example, in the following publications:

"McCutcheon's Detergents and Emulsifiers Annual", MC Publishing Corp., Glen Rock, N.J., USA, 1988, H. Stache, "Tensid-Taschenbuch", 2nd edition, C. Hanser Verlag, Munich, Vienna, 1981, M. and J. Ash, "Encyclopedia of Surfactants", Vol. I–III, Chemical Publishing Co., New York, 1980–1981.

The pesticidal compositions for crop protection usually comprise 0.1 to 99%, especially 0.1 to 95%, of a compound of formula I or formula Ia or combinations of that compound with other insecticides or acaricides, 1 to 99.9% of a solid or liquid adjuvant, and 0 to 25%, especially 0.1 to 25%, of a surfactant. Whereas commercial products will preferably be formulated as concentrates, the end user will normally employ dilute formulations comprising considerably lower active ingredient concentrations. Typical application concentrations are from 0.1 to 1000 ppm, preferably from 0.1 to 500 ppm. For crop protection, the rates of application per hectare are generally from 1 to 2000 g of active ingredient per hectare of cultivated area, preferably from 10 to 1000 g/ha, especially from 20 to 600 g/ha.

Preferred forms of administration to warm-blooded animals for controlling helminths include solutions, emulsions, suspensions (drenches), feed additives, powders and tablets, including effervescent tablets, boli, capsules and microencapsulations, it being necessary to take into account the physiological acceptability of the formulation adjuvants.

Suitable binders for tablets and boll are chemically modified natural polymer substances that are soluble in water or alcohol, such as starch, cellulose or protein derivatives (e.g. methylcellulose, carboxymethylcellulose, ethylhydroxyethylcellulose, proteins, such as zein, gelatin and the like) and synthetic polymers, such as, for example, polyvinyl alcohol, polyvinylpyrrolidone etc. The tablets also comprise fillers (e.g. starch, microcrystalline cellulose, sugar, lactose etc.), glidants and disintegrators.

If the anthelmindc compositions are in the form of feed concentrates, then the carriers used are, for example, performance feed, feed grain or protein concentrates. In addition to the active ingredients, such feed concentrates or compositions may contain additives, vitamins, antibiotics, chemotherapeutic agents, or other pesticides, especially bacteriostatics, fungistatics or coccidiostatics, or also hormone preparations, substances having an anabolic activity, or substances that promote growth, influence the meat quality of animals for slaughter or are useful to the organism in some other way. If the compositions or the active ingredients of formula I they comprise are added directly to the feed or to the herd drinks, then the prepared feed or the prepared drink preferably comprises the active ingredients in a concentration of from approximately 0.0005 to 0.02 percent by weight (5–200 ppm).

The compositions according to the invention can be administered to the animals to be treated perorally, parenterally or subcutaneously, the compositions being in the form of solutions, emulsions, suspensions (drenches), powders, tablets, boli and capsules.

The anthelmintic compositions according to the invention generally comprise from 0.1 to 99% by weight, preferably from 0.1 to 95% by weight, of a compound of formula I, Ia or mixtures thereof, from 99.9 to 1% by weight, preferably from 99.8 to 5% by weight, of a solid or liquid adjuvant, including from 0 to 25% by weight, preferably from 0.1 to 25% by weight, of a surfactant.

Whereas commercial products will preferably be formulated as concentrates, the end user will normally employ dilute formulations.

The compositions may also comprise further auxiliaries such as stabilisers, antifoams, viscosity regulators, binders, tackifiers as well as other active ingredients for obtaining special effects.

The present invention relates also to such anthelmintic compositions employed by the end user.

In each of the methods for pest control according to the invention and in each of the pesticides according to the invention the compound of formula I may be used in any of its structural configurations, in mixtures thereof or in the form of its salts.

The invention includes also a method for the prophylactic protection of warm-blooded animals, especially productive livestock, domestic animals and pets, against parasitic helminths, which comprises administering the compound of formula I or active ingredient formulations prepared therefrom to the animals in the form of an additive to the feed or to the drink or, alternatively, in solid or liquid form, orally, by means of injection or parenterally. The invention includes also the compounds according to the invention of formula I for use in one of the mentioned methods.

The Examples that follow serve merely to illustrate the invention without limiting the invention.

Preferred formulations have especially the following composition: (throughout, percentages are by weight)
Emulsifiable concentrates:
thiangazole 1 to 90%,
preferably 5 to 20%
surfactant: 1 to 30%,
preferably 10 to 20%
liquid carrier: 5 to 94%,
preferably 70 to 85%
Dusts:
thiangazole 0.1to 10%,
preferably 0.1 to 1%
solid carrier: 99.9 to 90%, preferably 99.9 to 99%
Suspension concentrates:
thiangazole 5 to 75%,
preferably 10 to 50%
water: 94 to 24%,
preferably 88 to 30%
surfactant: 1 to 40%,
preferably 2 to 30%
Wettable powders:
thiangazole 0.5 to 90%,
preferably 1 to 80%
surfactant: 0.5 to 20%,
preferably 1 to 15% solid carrier: 5 to 95%,
preferably 15 to 90%
Granules:
thiangazole 0.5 to 30%,
preferably 3 to 15%
solid carrier: 99.5 to 70%, preferably 97 to 85%

The compositions may also comprise further additives such as stabilisers, for example vegetable oils or epoxidised vegetable oils (epoxidised coconut oil, rapeseed oil or soybean oil), antifoams, for example silicone oil, preservatives, viscosity regulators, binders, tackifiers as well as fertilisers or other active ingredients for obtaining special effects.

The following Examples serve to illustrate the invention. They do not limit the invention.

D. Preliminary tests for biological activity

The antibiotic activity is determined by means of an agar diffusion test with reference to the inhibiting areola diameter, or from the culture density in a series dilution test. Thiangazole inhibits the growth of some fungi, for example *Mucor hiemalis, Botrytis cinerea Gibberella fujikuroi, Rhizopus arrhizus* and *Pythium debaryanum*. The MIC for Ustilago maydis is 3,2 μg/ml. In the case of sub-mitochondrial particles of deer heart, thiangazole inhibits NADH oxidation, Investigations by differential spectroscopy show complex I ($NADH_2$:ubiquinone-oxidoreductase) of the eukaryotic respiratory chain to be the site of action of thiangazole.

E. Formulation Examples

| E.1. Emulsifiable concentrates | a) | b) | c) |
| --- | --- | --- | --- |
| a compound of formula Ia | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| E.2. Emulsifiable concentrates | a) | b) | c) |
| --- | --- | --- | --- |
| a compound of formula Ia | 10% | 8% | 60% |
| octylphenol polyethylene glycol ether (4–5 moles of ethylene oxide) | 3% | 3% | 2% |
| calcium dodecylbenzenesulfonate | 3% | 4% | 4% |
| castor oil polyethylene glycol ether (35 moles of ethylene oxide) | 4% | 5% | 4% |
| cyclohexanone | 30% | 40% | 15% |
| xylene mixture | 50% | 40% | 15% |

Emulsions of any desired concentration can be produced from such concentrates by dilution with water.

| E.3. Suspension concentrate | |
| --- | --- |
| a compound of formula Ia | 40% |
| ethylene glycol | 10% |
| nonylphenol polyethylene glycol ether (15 moles of ethylene oxide) | 6% |
| sodium liposulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, affording a suspension concentrate from which suspensions of any desired concentration can be obtained by dilution with water.

| E.4. Water-dispersible powder mixtures | a) | b) | c) |
| --- | --- | --- | --- |
| a compound of formula Ia | 25% | 50% | 75% |
| sodium lignosulfonate | 5% | 5% | — |
| oleic acid | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

| E.5. Dusts | a) | b) |
| --- | --- | --- |
| a compound of formula Ia | 2% | 5% |
| highly dispersed silicic acid | 1% | 5% |
| talcum | 97% | — |
| kaolin | — | 90% |

Ready-for-use dusts are obtained by intimately mixing the carriers with the active ingredient and grinding the mixture.

| E.6. Granules | a) | b) |
| --- | --- | --- |
| a compound of formula Ia | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo. Such granules can be mixed with animal feed.

| E.7. Granules | |
| --- | --- |
| a compound of formula Ia | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| E.8. Granules | |
| --- | --- |
| a compound of formula Ia | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| E.9. Tablets or boli | | |
| --- | --- | --- |
| I | compound of formula Ia | 33.00% |
| | methylcellulose | 0.80% |

E.9. Tablets or boli

|    |                              |        |        |
|----|------------------------------|--------|--------|
|    | highly dispersed silicic acid | 0.80%  |        |
|    | cornstarch                   |        | 8.40%  |
| II | crystalline lactose          | 22.50% |        |
|    | cornstarch                   |        | 17.00% |
|    | microcrystalline cellulose   | 16.50% |        |
|    | magnesium stearate           | 1.00%  |        |

I The methylcellulose is stirred into water and allowed to swell; the silicic acid is stirred in and the mixture is made into a homogeneous suspension. The active ingredient and cornstarch are mixed and the aqueous suspension is incorporated into this mixture which is kneaded to a paste. The mass so obtained is granulated through a 12M sieve and dried.

II All four adjuvants are thoroughly mixed.

III The premixtures obtained in accordance with I and II are mixed and compressed to tablets or boli.

E.10. Injectable preparations

α. Oily vehicle (slow release)

| compound of formula Ia | 0.1–1.0 g |
|---|---|
| groundnut oil | ad 100 ml |
| compound of formula Ia | 0.1–1.0 g |
| sesame oil | ad 100 ml |

Preparation: The active ingredient is dissolved in some of the oil with stirring and if necessary with gentle heating. After cooling, the solution is made up to the desired volume and sterile-filtered through a suitable 0.22 μm membrane filter.

β. Water-miscible solvent (medium rate of release)

| compound of formula Ia | 0.1–1.0 g |
|---|---|
| 4-hydroxymethyl-1,3-dioxolane (glycerol formal) | 40 g |
| 1,2-propanediol | ad 100 ml |
| compound of formula Ia | 0.1–1.0 g |
| glycerol dimethylketal | 40 g |
| 1,2-propanediol | ad 100 ml |

Preparation: The active ingredient is dissolved in some of the solvent with stirring, made up to the desired volume and sterile-filtered through a suitable 0.22 μm membrane filter.

γ. Aqueous soluble preparation (rapid release)

| compound of formula Ia | 0.1–1.0 g |
|---|---|
| polyethoxylated castor oil (40 ethylene oxide units) | 10 g |
| 1,2-propanediol | 20 g |
| benzyl alcohol | 1 g |
| Aqua ad inject. | ad 100 ml |
| compound of formula Ia | 0.1–1.0 g |
| polyethoxylated sorbitan monooleate (20 ethylene oxide units) | 8 g |
| 4-hydroxymethyl-1,3-dioxolane (glycerol formal) | 20 g |
| benzyl alcohol | 1 g |
| Aqua ad inject. | ad 100 ml |

Preparation: The active ingredient is dissolved in the solvents and the surfactant, made up to the desired volume with water and then sterile-filtered through a suitable membrane filter having a pore diameter of 0.22 μm.

The aqueous systems can be used preferably also for oral and/or intraruminal administration.

F. Biological Examples

The anthelmintic activity is demonstrated by means of the following tests:

F.1. Trial with sheep infested with nematodes such as *Haemonchus contortus* and *Trichostrongylus colubriformis*

Thiangazole is administered in the form of a suspension using a stomach probe or by intraruminal injection to sheep that have previously been artificially infested with nematodes, such as *Haemonchus contortus* and *Trichostrongylus colubriformis*. 1 to 3 animals are used for each dose per trial. Each sheep is treated only once with a single dose.

A first evaluation is made by comparing the number of worm eggs excreted in the faeces of the sheep before and after treatment.

Seven to ten days after treatment the sheep are sacrificed and dissected. The evaluation is carried out by counting the worms remaining in the intestine after the treatment. Sheep simultaneously and similarly infested but untreated are used as a control or comparison.

A sharp reduction in nematode infestation is achieved with thiangazole in this trial. For example the use of 20 mg of active ingredient per kg of body weight effects virtually complete reduction of nematode infestation.

F.2. Trial with sheep infested with cestodes such as *Moniezia benedeni*

The active ingredient is administered in the form of a suspension using a stomach probe or by intraruminal injection to sheep that have previously been artificially infested with cestodes, such as *Moniezia benedeni*. 1 to 3 animals are used for each dose per trial. Each sheep is treated only once with a single dose. Seven to ten days after treatment the sheep are sacrificed and dissected. The evaluation is carried out by counting the worms remaining in the intestine after the treatment. Sheep simultaneously and similarly infested but untreated are used as a control or comparison. In this test thiangazole effects an approximately 90% reduction in cestode infestation at a dose of less than 20 mg/kg body weight.

F.3. Action against *Dermanyssus gallinae*

2 to 3 ml of a solution comprising 100 ppm of test compound, and approximately 200 mites at various stages of development, are placed in a glass container that is open at the top. The container is then closed with a cotton wool plug, shaken for 10 minutes until the mites are completely wetted, and then inverted for a short time so that the remaining test solution can be absorbed by the cotton wool. After 3 days, the mortality of the mites is determined as a percentage by counting the number of dead individuals. Thiangazole exhibits good activity against *Dermanyssus gallinae* in this test.

F.4. Action against *Lucilia sericata*

Freshly deposited eggs of the blow fly *Lucilia sericata* are introduced in small portions (30–50 eggs) into test tubes in which 4 ml of nutrient medium have previously been mixed with 1 ml of test solution in the intermediate dilution required for the final concentration. After inoculation of the culture medium the test tubes are closed with a cotton wool plug and incubated in an incubator at 30° C. for four days. By this time, larvae approximately 1 cm long (stage 3) have developed in the medium that, for comparison, has not been treated. If a compound is active, the larvae are at this time either dead or moribund and clearly retarded. The test is carried out simultaneously at concentrations of from 10–0.01 ppm. The activity is measured at the lowest fully active concentration (LC 100). The test includes both compounds that are effective by contact and those that are effective as an ingested poison. Repellence is also taken into account, since the larvae migrate from the medium and starve. Thiangazole exhibits full activity even at low concentrations in this test.

F.5. Action against *Lucilia cuprina*

Freshly deposited eggs of the blow fly species *Lucilia cuprina* are introduced in small portions (30–50 eggs) into test tubes in which 4 ml of nutrient medium have previously been mixed with 1 ml of test solution comprising 16 ppm of the test compound. After inoculation of the culture medium the test tubes are closed with a cotton wool plug and incubated in an incubator at 30° C. for four days. By this time, larvae approximately 1 cm long (stage 3) have developed in the untreated medium. If a compound is active the larvae are at this time either dead or clearly retarded. Evaluation is effected after 96 hours. Thiangazole exhibits very good activity against *Lucilia cuprina*.

F.6.Trial with sheep infested with *Fasciola hepatica*

The active ingredient is administered in the form of a suspension using a stomach probe or by intraruminal injection to sheep that have previously been artificially infested with *Fasciola hepatica*. 3 animals are used for each dose per trial. Each animal is treated only once with a single dose.

A first evaluation is made by comparing the number of worm eggs excreted in the faeces of the sheep before and after treatment.

Three to four weeks after treatment the sheep are sacrificed and dissected. The evaluation is carried out by counting the liver flukes remaining in the gall-bladder ducts after treatment. Sheep simultaneously and similarly infested but untreated are used as a control or comparison. The difference in the number of liver flukes counted in the two groups gives the degree of effectiveness of the test compound.

Thiangazole exhibits good activity against *Fasciola hepatica* at doses of less than 50 mg of active ingredient/kg of body weight in this test.

F.7. Ovicidal/larvicidal action against *Heliothis virescens*

Egg deposits of *Heliothis virescens* on cotton are sprayed with an aqueous emulsion comprising 400 ppm of test compound. 8 days later, the percentage of eggs which have hatched and the survival rate of the caterpillars are evaluated in comparison with untreated controls (% reduction in the population). Thiangazole exhibits good activity against *Heliothis virescens* in this test.

F.8.Action against *Aphis craccivora*

Pea seedlings are infested with *Aphis craccivora* and then sprayed with a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants. Thiangazole exhibits good activity against *Aphis craccivora* in this test.

F.9.Action against *Tetranychus urticae*

Young bean plants are populated with a mixed population of *Tetranychus urticae* and sprayed one day later with an aqueous emulsion comprising 400 ppm of the test compound. The plants are then incubated for 6 days at 25° C. and then evaluated. The percentage reduction in the population (% activity) is determined by comparing the number of dead eggs, larvae and adults on the treated plants with that on untreated plants. Thiangazole exhibits good activity against *Tetranychus urticae* in this test.

F.10.Action against *Heliothis virescens* caterpillars

Young soybean plants are sprayed with an aqueous emulsion comprising 400 ppm of the test compound. After the spray coating has dried, the soybean plants are populated with 10 *Heliothis virescens* caterpillars in the first stage and placed in a plastics container. Evaluation is made 6 days later. The percentage reduction in the population or the percentage reduction in feeding damage. (% activity) is determined by comparing the number of dead caterpillars and the feeding damage on the treated plants with that on untreated plants. Thiangazole exhibits very good activity against *Heliothis virescens* caterpillars.

F.11Action against *Plutella xylostella* caterpillars

Young cabbage plants are sprayed with an aqueous emulsion comprising 400 ppm of the test compound. After the spray coating has dried, the cabbage plants are populated with 10 *Plutella xylostella* caterpillars in the third stage and placed in a plastics container. Evaluation is made 3 days later. The percentage reduction in the population or the percentage reduction in feeding damage (% activity) is determined by comparing the number of dead caterpillars and the feeding damage on the treated plants with that on untreated plants. Thiangazole exhibits good activity against *Plutella xylostella* in this test. The activity is over 80%.

What is claimed is:

1. A pesticidal composition comprising a pesticidally-effective amount of a compound having the absolute configuration represented by formula 1a

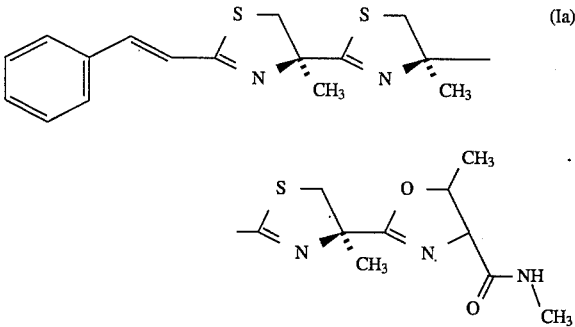

and a suitable carrier.

2. A method of protecting plants from arthropods or insects, which method comprises applying to the plants or a locus thereof an effective amount of the pesticidal composition of claim 1.

3. A method of killing arthropods or insects, which method comprises applying to the arthropods or insects an effective amount of the pesticidal composition of claim 1.

* * * * *